(12) United States Patent
Haytman et al.

(10) Patent No.: US 8,980,174 B2
(45) Date of Patent: Mar. 17, 2015

(54) METHODS AND APPARATUS FOR REDUCING COUNT OF INFECTIOUS AGENTS IN INTRAVENOUS ACCESS SYSTEM

(75) Inventors: Eyal Haytman, Kfar Vradim (IL); Assaf Deutsch, Tzafariya (IL); Eliahu Pewzner, Modi'in Ilit (IL)

(73) Assignee: Bactriblue, Ltd., Holon (IL)

( * ) Notice: Subject to any disclaimer, the term of this patent is extended or adjusted under 35 U.S.C. 154(b) by 416 days.

(21) Appl. No.: 13/513,975

(22) PCT Filed: May 11, 2012

(86) PCT No.: PCT/US2012/037533
§ 371 (c)(1),
(2), (4) Date: Jun. 5, 2012

(65) Prior Publication Data
US 2013/0303972 A1 Nov. 14, 2013

Related U.S. Application Data

(60) Provisional application No. 61/485,926, filed on May 13, 2011.

(51) Int. Cl.
*A61L 2/08* (2006.01)
(52) U.S. Cl.
USPC .............................. 422/22; 604/21
(58) Field of Classification Search
CPC ................... A61N 5/06; A61M 25/00
USPC .................. 422/22; 604/21; 607/88
See application file for complete search history.

(56) References Cited

U.S. PATENT DOCUMENTS

| | | |
|---|---|---|
| 4,412,834 A | 11/1983 | Kulin |
| 4,910,942 A | 3/1990 | Dunn et al. |
| 4,930,504 A | 6/1990 | Diamantopoulos et al. |
| 5,474,528 A | 12/1995 | Meserol |
| 5,620,478 A | 4/1997 | Eckhouse |
| 5,634,711 A | 6/1997 | Kennedy et al. |

(Continued)

FOREIGN PATENT DOCUMENTS

| | | |
|---|---|---|
| WO | 9502324 A1 | 1/1995 |
| WO | 2004014487 A1 | 2/2004 |
| WO | 2008066943 A2 | 6/2008 |

OTHER PUBLICATIONS

Int'l Search Report and Written Opinion, Int'l Application No. PCT/IB2012/001898, dated Jan. 24, 2013.

(Continued)

*Primary Examiner* — Sean E Conley
(74) *Attorney, Agent, or Firm* — Ostrager Chong Flaherty & Broitman P.C.

(57) ABSTRACT

The device disclosed herein may be affixed over a transparent dressing overlying the catheter entry point, or may be used independent of such a dressing. The device may be affixed to the catheter insertion site using an adhesive or fastening band, or through other methods. Depending on context, the device may be used continuously or periodically, and may be affixed such that it is directly abutting a transparent dressing or directly adjacent to the skin surface, or it may be spaced a certain distance from the skin. If spaced from the skin, light may be directed from the light sources, either directly or indirectly through optical conduits. Preferably the light sources will be positioned such that light from the light sources overlaps at one or more areas on the skin, especially the catheter entry point.

26 Claims, 8 Drawing Sheets

(56) References Cited

U.S. PATENT DOCUMENTS

| | | |
|---|---|---|
| 5,766,233 A | 6/1998 | Thiberg |
| 5,843,143 A | 12/1998 | Whitehurst |
| 5,944,748 A | 8/1999 | Mager et al. |
| 6,045,575 A | 4/2000 | Rosen et al. |
| 6,107,466 A | 8/2000 | Hasan et al. |
| 6,156,028 A | 12/2000 | Prescott |
| 6,183,500 B1 | 2/2001 | Kohler |
| 6,223,071 B1 | 4/2001 | Lundahl et al. |
| 6,267,779 B1 | 7/2001 | Gerdes |
| 6,379,376 B1 | 4/2002 | Lubart |
| 6,443,978 B1 | 9/2002 | Zharov |
| 6,454,791 B1 | 9/2002 | Prescott |
| 6,461,568 B1 | 10/2002 | Eckhardt |
| 6,551,346 B2 | 4/2003 | Crossley |
| 6,663,659 B2 | 12/2003 | McDaniel |
| 6,835,202 B2 | 12/2004 | Harth et al. |
| 6,887,260 B1 | 5/2005 | McDaniel |
| 7,001,413 B2 | 2/2006 | Butler |
| 7,077,544 B2 | 7/2006 | Parker |
| 7,116,554 B2 | 10/2006 | Lee et al. |
| 7,198,634 B2 | 4/2007 | Harth et al. |
| 7,305,163 B2 | 12/2007 | Williams |
| 7,517,101 B2 | 4/2009 | Tobin |
| 7,686,839 B2 | 3/2010 | Parker |
| 2003/0031586 A1 | 2/2003 | Eckhardt |
| 2003/0221687 A1 | 12/2003 | Kaigler |
| 2004/0034397 A1 | 2/2004 | Lin |
| 2004/0034398 A1 | 2/2004 | Eckhardt et al. |
| 2004/0092890 A1 | 5/2004 | Ash |
| 2004/0166129 A1 | 8/2004 | Clement et al. |
| 2005/0055070 A1 | 3/2005 | Jones et al. |
| 2006/0085052 A1 | 4/2006 | Feuerstein et al. |
| 2006/0207267 A1 | 9/2006 | Erdman |
| 2006/0216193 A1 | 9/2006 | Johnson |
| 2008/0027399 A1 | 1/2008 | Harding |
| 2008/0051736 A1 | 2/2008 | Rioux |
| 2008/0104978 A1 | 5/2008 | Kim |
| 2009/0130169 A1 | 5/2009 | Bernstein |

OTHER PUBLICATIONS

Written Opinion of the International Searching Authority, mailed Aug. 10, 2011 in International Application No. PCT/IL11/00244.

Elman et al., Abstract of: The effective treatment of acne vulgaris by a high-intensity, narrow band 405-420 nm light source, Journal of Cosmetic and Laser Therapy, vol. 5, issue 2, pp. 111-117 (2003).

Raad et al., Ultrastructural Analysis of Indwelling Vascular Catheters: A Quantitative Relationship between Luminal Colonization and Duration of Placement, The Journal of Infectious Diseases; 168:400-7 (1993).

Raad, Intravascular-catheter-related infections, The Lancet, vol. 351, 893-98 (1998).

Mermel, New Technologies to Prevent Intravascular Catheter-Related Bloodstream Infections, Emerging Infectious Diseases, vol. 7, No. 2, pp. 197-199 (2001).

Guffey et al., Effects of Combined 405-nm and 880-nm Light on *Staphylococcus aureus* and *Pseudomonas aeruginosa* in Vitro, Photomedicine and Laser Surgery, vol. 24, No. 6, pp. 680-683 (2006).

Fukui et al., Specific-wavelength visible light irradiation inhibits bacterial growth of *Porphyromonas gingivalis* Journal of Periodontal Research, vol. 43, pp. 174-178 (2008).

Enwemeka et al., Visible 405 nm SLD Light Photo-Destroys Methicillin-Resistant *Staphylococcus aureus* (MRSA) In Vitro, Laser in Surgery and Medicine, 40:734-747 (2008).

Elliott et al., Novel Approach to Investigate a Source of Microbial Contamination of Central Venous Catheters, Eur. J. Clin Microbiol Infect. Dis., vol. 16, No. 3, pp. 210-213 (1997).

SwabCap Luer Access Valve Disinfection Cap, Excelsior Medical Corporation, www.excelsiormedical.com/swabcap.php, Mar. 3, 2010.

Baxter U.S.—Healthcare professional, V-LINK Luer-Activated Device with VITALSHIELD Protective Coating, www.baxtercom/healthcare_professionals/products/vlink.html, Jul. 8, 2010.

Guffey et al., In Vitro Bactericidal effects of 405-nm and 470-nm Blue Light, Photomedicine and Laser Surgery, vol. 24, No. 6, pp. 684-688 (2006).

Elcam Medical Inc., www.devicelink.com/company98/co/171/17118.html, Mar. 19, 2010.

Peterson, Central Line Sepsis, Clinical Journal of Oncology Nursing, vol. 7, No. 2, pp. 218-221 (2003).

Elcam Medical, B-Stop Whitepaper, Rev. 5, May 2007.

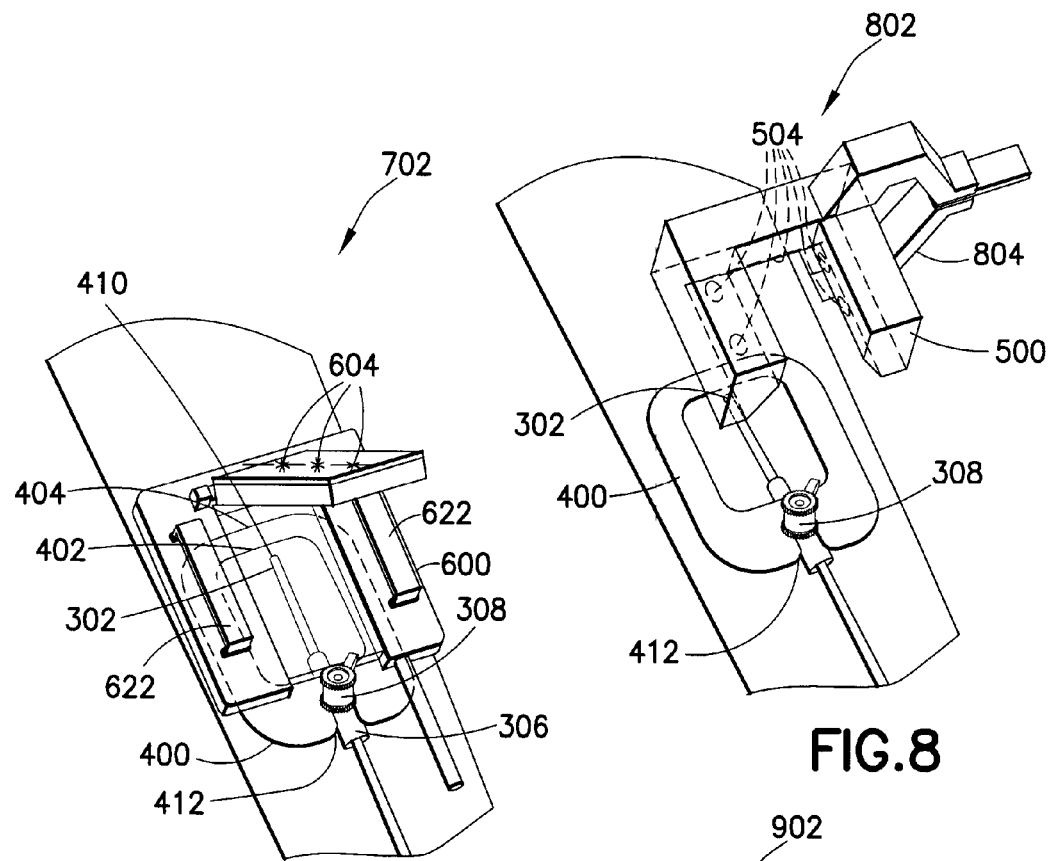
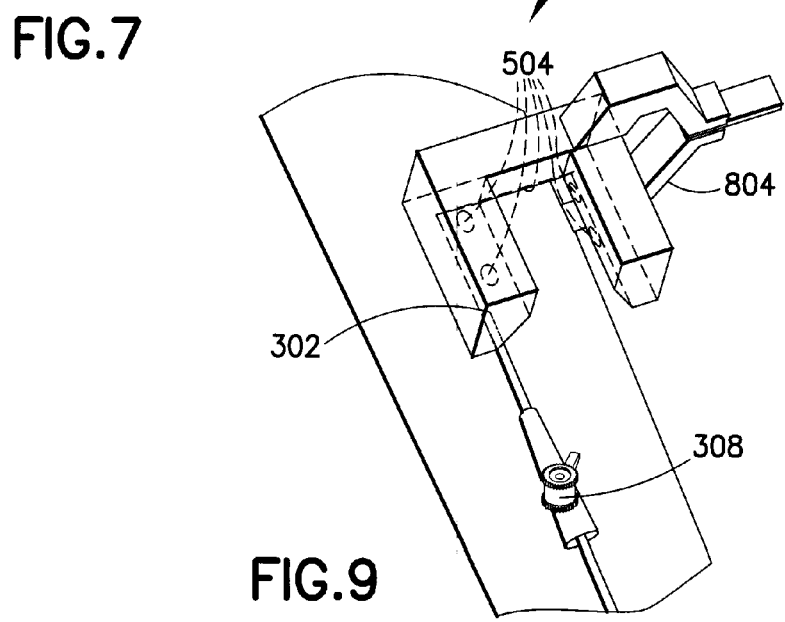

METHODS AND APPARATUS FOR REDUCING COUNT OF INFECTIOUS AGENTS IN INTRAVENOUS ACCESS SYSTEM

This application is a U.S. National Stage of International Application No. PCT/US2012/037533 filed May 11, 2012, which claims priority to U.S. Provisional Application No. 61/485,926 filed May 13, 2011, both applications of which are incorporated by reference herein in their entireties.

BACKGROUND

This invention generally relates to methods and systems for reducing the risk of patient bloodstream infection by microorganisms during administration of various medications and fluids through lines. In particular, the invention relates to methods and systems for reducing the count of infectious agents and inhibiting the growth of microorganisms in the vicinity of the point of entry of a catheter into a patient's body.

It is a common practice in medicine to administer various medications and fluids into and withdraw blood from a patient's vascular system. For these purposes, various intravenous access devices exist. Such a device typically has a hollow needle, the tip of which is inserted into a patient's blood vessel for variable periods of time—from seconds (for example, injections and blood sampling) to a year (for example, total parenteral nutrition, chemo-therapy and dialysis). All such devices bypass several natural anti-infection defense barriers and introduce a risk of direct bloodstream contamination. The general terms for these devices is "lines." The type of infection that arises from the use of such "lines" is called "line sepsis." Elaborate and complicated precautions and prevention techniques are in use, and include use of one or more of the following means: sterile equipment, sterile insertion technique, aseptic handling techniques, replacement of the "lines" as indicated by various protocols, antibiotics, and antibacterial substances impregnated into catheters.

One of the unsolved problems that is especially relevant to intravascular catheters with longer time of use is colonization by microorganisms of the area in the immediate vicinity of the point of entry of the catheter into the body. Various means are presently used to maintain sterility of a catheter insertion site. For example, once an intravenous access device is inserted into a blood vessel, a dressing is applied to the area around the insertion site. The dressing provides a physical barrier to prevent contamination of the site by infectious agents.

Dressings are periodically changed. Care is needed to ensure that infectious agents do not contaminate the site. For example, during a dressing change, an antiseptic wipe may be used to sterilize the insertion site. Other materials used for changing a dressing, such as gloves and wipes, must also be sterile.

These methods of cleaning and disinfecting the area around the point of insertion of a catheter into a patient's body are of low efficacy. Decontamination of indwelling devices may also be problematic because the patient, his blood, and the administered medicine are potentially exposed to all of the physical, chemical and pharmacological effects of such decontamination.

There is a need for improved apparatus and improved methods for reducing the risk of patient bloodstream infection by microorganisms which may contaminate the catheter insertion area.

BRIEF SUMMARY

The present invention is directed to methods, systems and devices for reducing catheter-related bloodstream infections. The technology disclosed herein starts fighting the bacteria immediately, at the point of insertion of a catheter into a human body, thereby stopping bacteria proliferation at an early stage.

Recent photobiology research has shown that various types of microorganisms can be eradicated by irradiation with visible light, especially in the "violet/blue spectral region." As used herein, the term "violet/blue spectral region" refers to blue light comprising wavelengths in the range of 455-492 nm and violet light comprising wavelengths in the range of 390-455 nm, consistent with the definitions of "blue" and "violet" given in the Academic Press Dictionary of Science and Technology, Harcourt Brace Jovanovich, New York (1992). The various bactericidal devices disclosed herein each comprise a light source that preferably emits light having wavelengths in the violet/blue spectral region.

The apparatus and methods disclosed herein can prevent patient bloodstream infection by microorganisms during administration of various medications or fluids via a catheter. In particular, the invention reduces contamination by microorganisms by means of irradiation with violet and/or blue light. Each of the embodiments disclosed herein comprises a source of violet and/or blue light installed such that light from the light source is directed toward a point of entry of a catheter into a human body. Preferably, a light-emitting diode or a laser diode that emits light in the desired wavelength (i.e., in the violet/blue spectral region) can be used.

One aspect of the invention is a method for reducing the count of infectious agents at a catheter entry point, comprising the following steps: (a) placing an optical element so that any transmitted light will be directed toward the point of catheter entry; (b) optically coupling the optical element to a source of light; and (c) causing the light source to emit light, the emitted light being transmitted by the optical element toward the catheter entry point, wherein the emitted light has a bactericidal effect.

Another aspect of the invention is a system for reducing the count of infectious agents at a catheter entry point, comprising: an optical element placed so that transmitted light will be directed toward the catheter entry point; and a source of light optically coupled to the optical element, wherein when the light source emits light, the emitted light is transmitted by the optical element toward the catheter entry point, wherein the emitted light has a bactericidal effect.

A further aspect of the invention is a system comprising a device consisting of a holder or housing having light sources emitting light having wavelengths in the range of 390-492 nm. The device is affixed to or supported near the catheter insertion site and is positioned such that light from the light sources is incident on the area of the skin in the immediate vicinity of the area of catheter insertion.

The device disclosed herein may be affixed over a transparent dressing overlying the catheter entry point, or may be used independent of such a dressing. The device may be affixed to the catheter insertion site using an adhesive or fastening band, or through other methods. Depending on context, the device may be used continuously or periodically, and may be affixed such that it is directly abutting a transparent dressing or directly adjacent to the skin surface, or it may be spaced a certain distance from the skin. If spaced from the skin, light may be directed from the light sources, either directly or indirectly through optical conduits. Preferably the light sources will be positioned such that light from the light sources overlaps at one or more areas on the skin, especially the catheter entry point.

Other aspects of the invention are disclosed below.

BRIEF DESCRIPTION OF THE DRAWINGS

FIG. 7 is a drawing showing a perspective view of a catheter insertion site contamination reduction device as applied directly to a transparent window dressing.

FIG. 8 is a drawing showing a perspective view of a catheter insertion site contamination reduction device spaced apart from, and illuminating, a transparent window dressing.

FIG. 9 is a drawing showing a perspective view of a catheter insertion site contamination reduction device spaced apart from and illuminating a catheter insertion site directly, without the use of a transparent window dressing.

Reference will now be made to the drawings in which similar elements in different drawings bear the same reference numerals.

DETAILED DESCRIPTION

Figure 1:
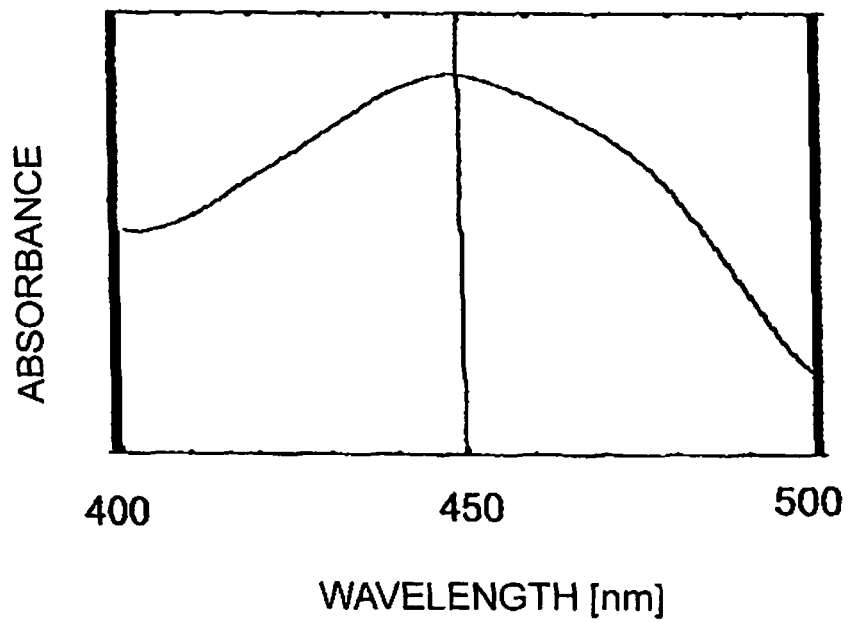
FIG. 1 is a graph showing a typical absorption band of flavin-adenine dinucleotide (FAD).

Recent photobiology research has showed that various types of microorganisms can be eradicated by irradiation of visible light, especially light in the violet/blue spectral region. The photo-contamination reduction effect has been shown for both in vivo and in vitro setups.

Elman et al. [see Elman, M., et al., "The effective treatment of acne vulgaris by a high-intensity, narrow band 405-420 nm light source," J. Cosmetic and Laser Therapy, 5(2), pp. 111-117 (June 2003)] applied narrow-band light at 405-420 nm for treatment of acne vulgaris. Recently the FDA approved narrow-band, high-intensity light therapy for treating acne. Light works by killing the acne-causing bacteria, *P. acnes*, and is being used to treat inflammatory acne vulgaris that has not responded to other acne therapies. Current light products do not contain ultraviolet (UV) light, which was a staple of former light therapy used to treat acne. UV light can damage skin and is no longer used to treat acne.

Enwemeka et al. [see Enwemeka, C. S., Williams, D., Hollosi, S., Yens, D., and Enwemeka, S. K., "Visible 405 nm SLD light photo-destroys methicillin-resistant *Staphylococcus aureus* (MRSA) in vitro," Lasers Surg. Med., 40(10), pp. 734-737 (December 2008)] studied the photo-sterilization effect of light at 405 nm on methicillin-resistant *Staphylococcus aureus* (MRSA) in vitro. According to Enwemeka et al., maximum eradication of the US-300 (92.1%) and the IS-853 colonies (93.5%) was achieved within 9.2 and 8.4 minutes of exposure, respectively. According to the authors, the effect was non-linear as increases of energy densities between 1.0 and 15 $J/cm^2$ resulted in more bacteria death than similar increases between 15 and 60 $J/cm^2$.

Fukui et al. [see Fukui, M., Yoshioka, M., Satomura, K., Nakanishi, H., and Nagayama, M., "Specific-wavelength visible light irradiation inhibits bacterial growth of *Porphyromonas gingivalis*," J. Periodontal Res., 43(2), pp. 174-178 (April 2008)] showed that the growth of *Porphyromonas gingivalis* bacteria irradiated at 400 and 410 nm was significantly suppressed compared with a nonirradiated control, whereas wavelengths of 430 nm and longer produced no significant inhibition. A constant energy density of 15 $J/cm^2$ was found to be enough to show an inhibitory effect. Significant inhibition of bacterial growth was found after only 1 min at 50 $mW/cm^2$ irradiation.

Guffey et al. [see Guffey, J. S., and Wilbom, J., "In vitro bactericidal effects of 405-nm and 470-nm blue light," Photomed. Laser Surg., 24(6), pp. 684-688 (December 2006)] showed that both 405-nm and 470-nm irradiation have a bactericidal effect on *Staphylococcus aureus* and *Pseudomonas aeruginosa* bacteria in vitro. The 405-nm light produced a dose-dependent bactericidal effect on *Pseudomonas aeruginosa* and *Staphylococcus aureus* ($p<0.05$), achieving a kill rate of 95.1% and nearly 90%, respectively. The 470-nm light effectively killed *Pseudomonas aeruginosa* at all dose levels, but only killed *Staphylococcus aureus* at 10 and 15 $J/cm^2$. With this wavelength, as much as 96.5% and 62% reduction of *Pseudomonas aeruginosa* and *Staphylococcus aureus* was achieved, respectively. Neither of the two wavelengths proved to be bactericidal with respect to anaerobic *Propionibacterim acnes*.

Guffey et al. [see Guffey, J. S., and Wilborn, J., "Effects of combined 405-nm and 880-nm light on *Staphylococcus aureus* and *Pseudomonas aeruginosa* in vitro," Photomed. Laser Surg., 24(6), pp. 680-683 (December 2006)] showed that combined irradiation of *Staphylococcus aureus* by 405 and 800 nm has a bactericidal effect.

The mechanisms involved in the photo-contamination reduction effect of blue/violet light are still a subject for numerous research efforts. The violet light in the 400-420 nm wavelength range interacts with the Soret absorption band of porphyrins. The higher wavelength blue light around 440-480 nm interacts with absorption band of flavins and riboflavine. The longer wavelength white light and near infra-red (NIR) light interact with cytochromes and higher absorption bands of porphyrins. The absorbed light excites these photosensitizers while subsequent relaxation from the excited state occurs by transferring electrons to $O_2$, thereby generating reactive oxygen species (ROS). When the ROS reach some increased value, they destroy the cell. The phenomenon is known as phototoxicity.

The present invention enables the provision of systems and methods for continuous (during use) contamination reduction of the area around the point of insertion of a catheter into a human body. The various embodiments of the invention are designed to illuminate this area with light having wavelengths in the range of 390-492 nm and emitted by low-cost light sources such as light-emitting diodes (LEDs) or laser diodes.

As used herein, the terms "light-emitting diode" and "laser diode" refer to devices comprising a semiconductor diode and an optical element optically coupled to that diode for shaping the radiation pattern of the light emitted by the diode. As used herein, the terms "light-emitting diode assembly" (or "LED assembly") and "laser diode assembly" refer to assemblies comprising either an LED or a laser diode mounted on or embedded within control circuitry.

Figure 2:
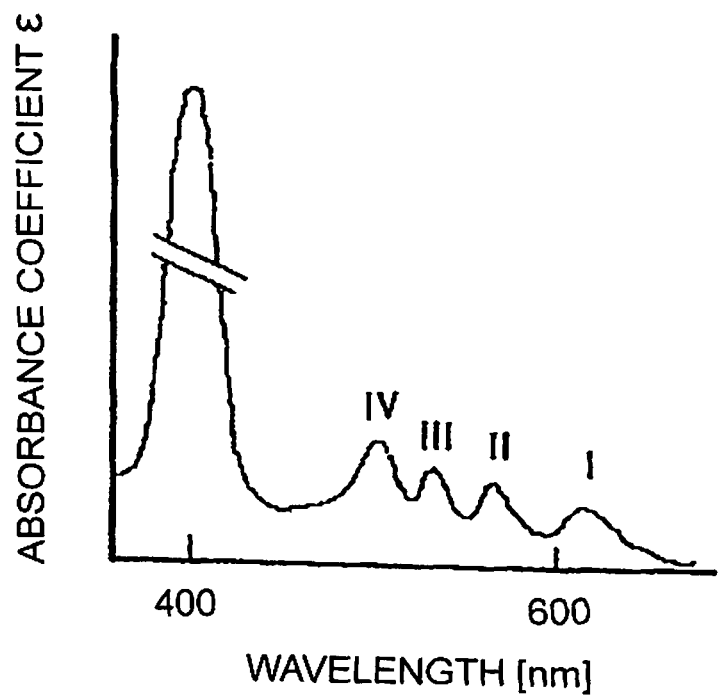
FIG. 2 is a graph showing a typical absorption band of porphyrins.
Figure 3:
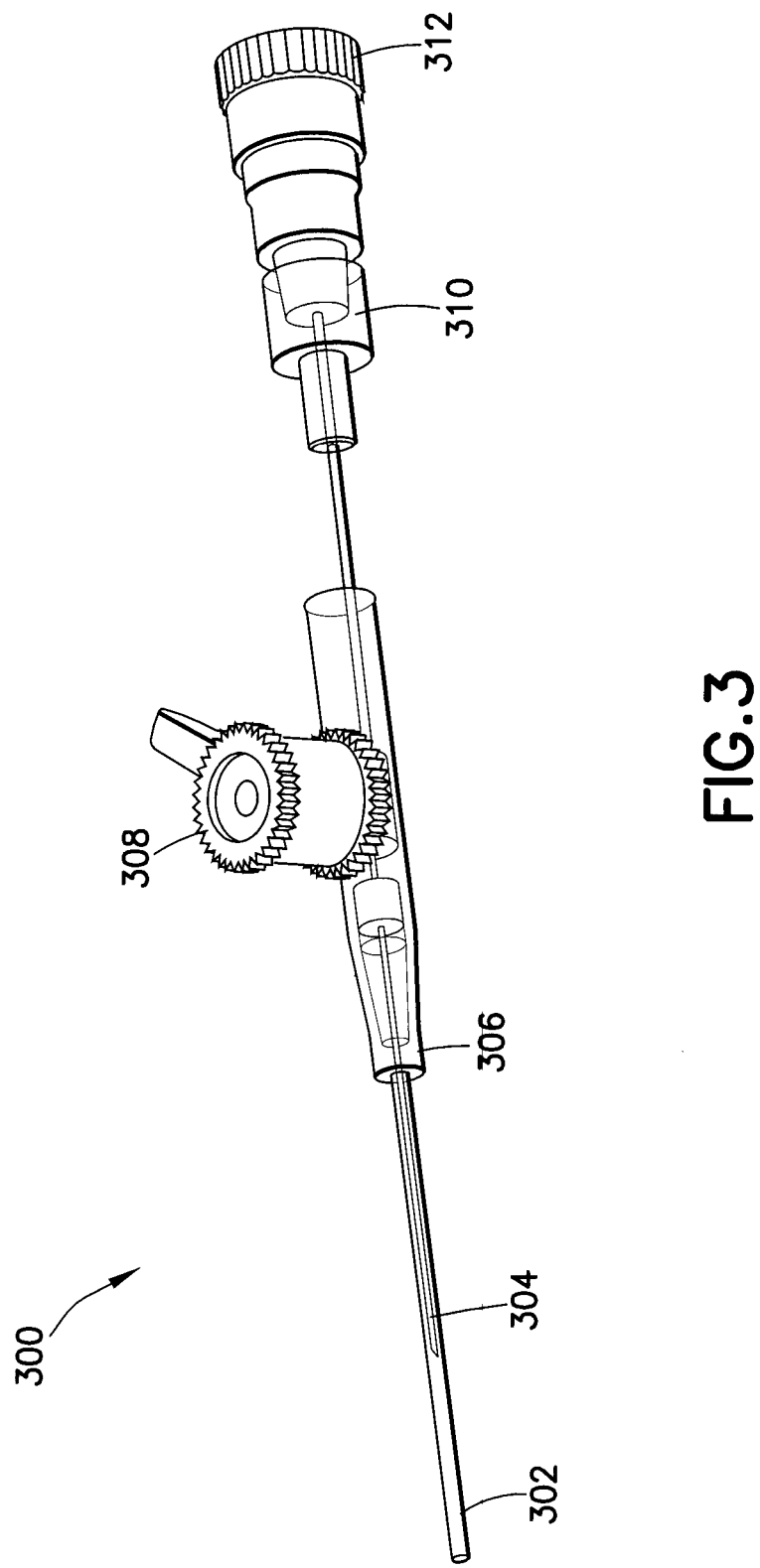
FIG. 3 is a drawing showing a perspective view of a typical peripheral venous catheter.

The absorption band of flavins [i.e., flavin-adenine dinucleotide (FAD)] is shown in FIG. 1. It is a relatively wide band at 450 nm with a full width at half maximum (FWHM) of about 100 nm. The typical absorption band of porphyrins is shown in FIG. 2. The absorption band for porphyrins comprises a very high Soret absorption band at about 400-410 nm and several smaller absorption Q-Bands (I-IV) along the visible and red parts of the spectrum. FIG. 3 shows the emission bands of commercially available high-power blue and violet LEDs. These LEDs are available from such well-known producers as Cree, Inc. and LumiLEDs in the U.S.A. and Semi-LED in Taiwan. In order to be effective for the contamination reduction of in-line catheters and tubing, the emission of the high-power LED should be optimized in such way that the emission band of the LED will overlap the absorption bands of porphyrins and/or FAD. Another possible light source is a laser diode. Laser diodes at wavelengths such as 400-410 nm and 440-450 nm are available from Nichia in Japan.

A typical catheter 300 is shown in FIG. 3. The type shown in this figure is a peripheral venous catheter although it is contemplated that the teachings of this disclosure may be applied to any catheter inserted through a patient's skin. The peripheral venous catheter 300 comprises a catheter tube ("cannula") 302 for insertion into a vein, a guiding needle 304 for facilitating cannula entry, a central tube 306, an auxiliary valve 308, an end tube 310 and a cap 312.

Risks associated with catheters include infection, due to continued presence of a foreign body in a blood vessel, and due to continued presence of an opening in the skin. To reduce these risks, a dressing is typically placed over the catheter insertion site. The dressing may be a traditional dressing, or may be a transparent, semipermeable dressing, such as Tegaderm™ brand dressings from 3M of St. Paul, Minn., USA.

Embodiments of the invention described herein utilize a housing having light-emitting elements for irradiating a catheter insertion site with light having wavelengths in a specific anti-microbial range. The transparency of the transparent dressing described above in the visible part of the spectrum allows violet and/or blue light to be transmitted through these materials from a LED or laser chip to the location of potential microorganism contamination. Although some attenuation of the violet and/or blue light in the elastomer material occurs, such attenuation is not so great (since the optical path is a few millimeters in most cases) as to interfere with delivery of the level of irradiation with violet and/or blue light required to effectively target the contamination reduction site.

Similar transmission cannot be achieved with UV light, which is highly absorbed in the plastics, so the same contamination reduction effect cannot be achieved using UV LEDs: UV light propagating into transparent window material will be immediately attenuated and therefore be practically ineffective. On the other side of the spectrum, the green, red or NIR LEDs will be much less effective since, as shown in FIGS. 1 and 2, the absorption of FAD and porphyrins at these wavelengths is much lower and therefore these wavelengths are less effective for contamination reduction through such a transparent dressing window.

An additional advantage of contamination reduction of human skin in the vicinity of the catheter needle insertion point through a transparent dressing window is human safety. The violet and/or blue light is safe to medical personnel and patients, whereas a similar device based on UV irradiation would be unsafe for the users.

Figure 4:
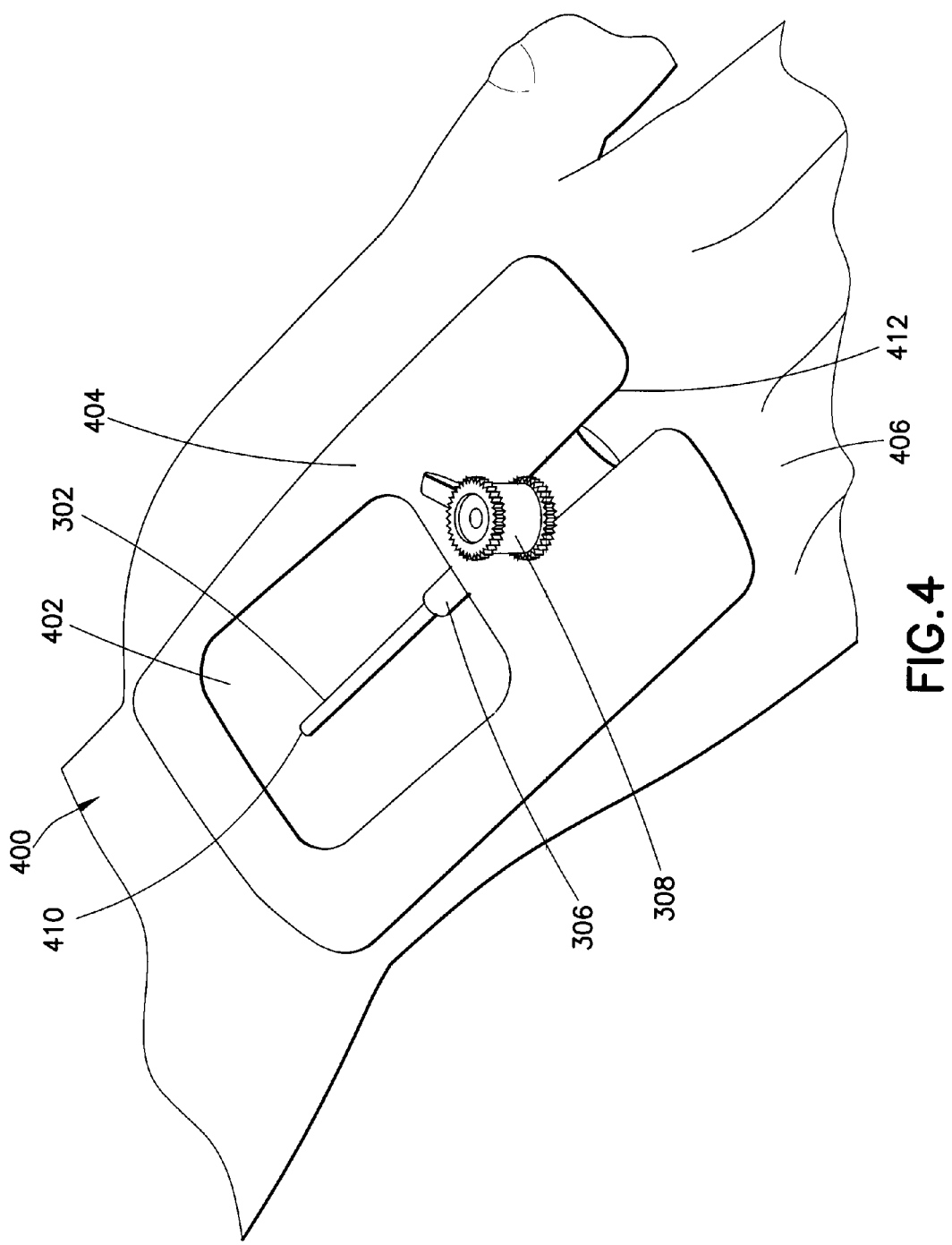
FIG. 4 is a drawing showing a perspective view of a typical transparent window dressing as applied to a catheter insertion site in a human hand.

As shown in FIG. 4, a typical transparent window dressing 400 for a catheter tube insertion site comprises a transparent window material 402 adhered to a frame 404. The dressing 400 is applied to an area 406 of a human body into which a catheter tube 302 has been inserted. The area 406 shown in FIG. 4 is the back of a hand. The window material 402 of the dressing 400 is positioned such that the catheter insertion point 410 is viewable through the window, allowing visual inspection of the insertion site without the necessity of removal of the dressing 400. Additional information about typical transparent window dressings may be found in U.S. Pat. No. 6,685,682 to Heinecke et al.

Figure 5A:
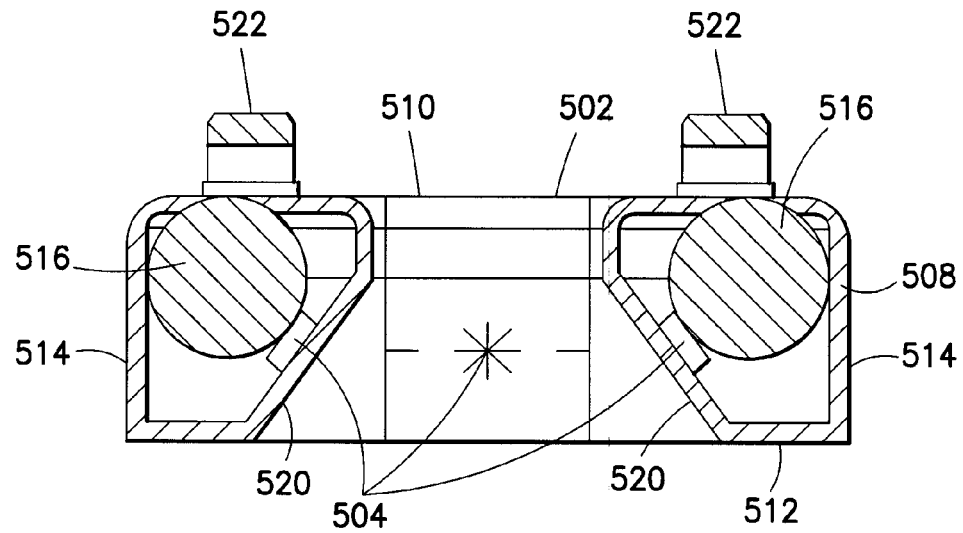
FIG. 5A is a drawing showing a side view of a first embodiment of a catheter insertion site contamination reduction device.
Figure 5B:
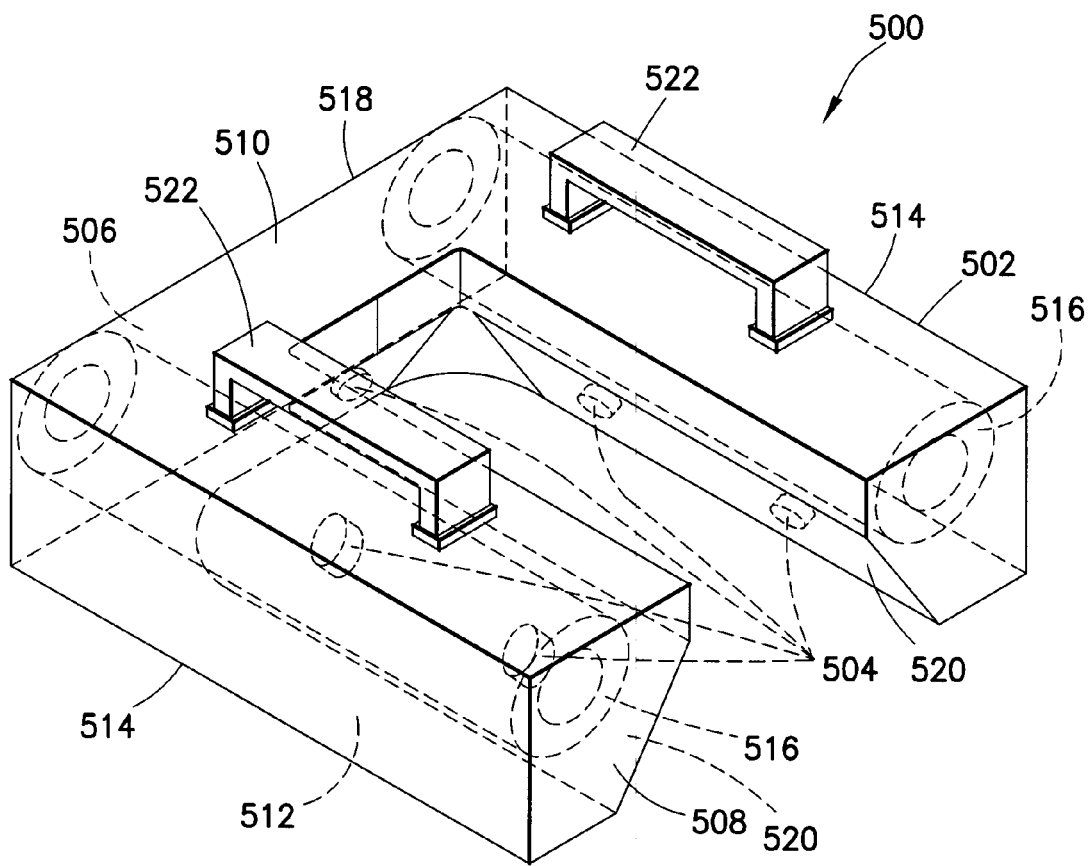
FIG. 5B is a drawing showing a perspective view of a first embodiment of a catheter insertion site contamination reduction device.

According to an embodiment of the present invention shown in FIGS. 5A and 5B, a catheter insertion site contamination reduction device 500 possesses a U-shaped housing 502 having one or more high-power LEDs or laser diodes 504 that emit light in the violet/blue spectral region. The U-shaped housing 502 has a first end 506, a second end 508, a top side 510 and a bottom side 512. Electronics (not shown) for controlling and powering LEDs 504 may be stored within the housing at the first end 506, and the LEDs 504 are positioned on the housing 502 such that they may emit light in a direction below the housing 502 while operational. Electronics may contain circuit elements to direct power provided from outside the device, or from batteries 516, to the LEDs 504. If power is provided from outside the device, an electronic cable (not shown in FIG. 5A or 5B) may be connected to the first end 506.

As shown in FIGS. 5A and 5B, the LEDs 504 are located within arms 514 and cross-bar 518. The LEDs 504 may be set deep into the body of the housing 502, may be positioned close to the surface of the housing 502, or may be attached to and protrude from the surface of the housing 502. The LEDs should be positioned such that light emitted from the LEDs 504 is directed towards a catheter insertion site located underneath the device 500 while the device 500 is in an installed configuration. Arms 514 therefore may have angled surfaces 520 that point the attached LEDs towards a central area below the housing 502. Although described above as U-shaped, the housing 502 need not have such a shape, and can be in any other shape, such as a square, rectangular, ovular or circular shape.

The device 500 may have power and control electronics to provide power to light-emitting elements 504 and to allow control of the device, including switching the light-emitting elements 504 on, timing controls for the light-emitting elements 504, and other necessary control functions. The device 500 may have attachment hooks 522 for holding straps 624 (omitted from FIGS. 5A and 5B for clarity, but shown in FIGS. 10A and 10B), used to secure the device 500 to a location on a patient's body.

Figure 6:
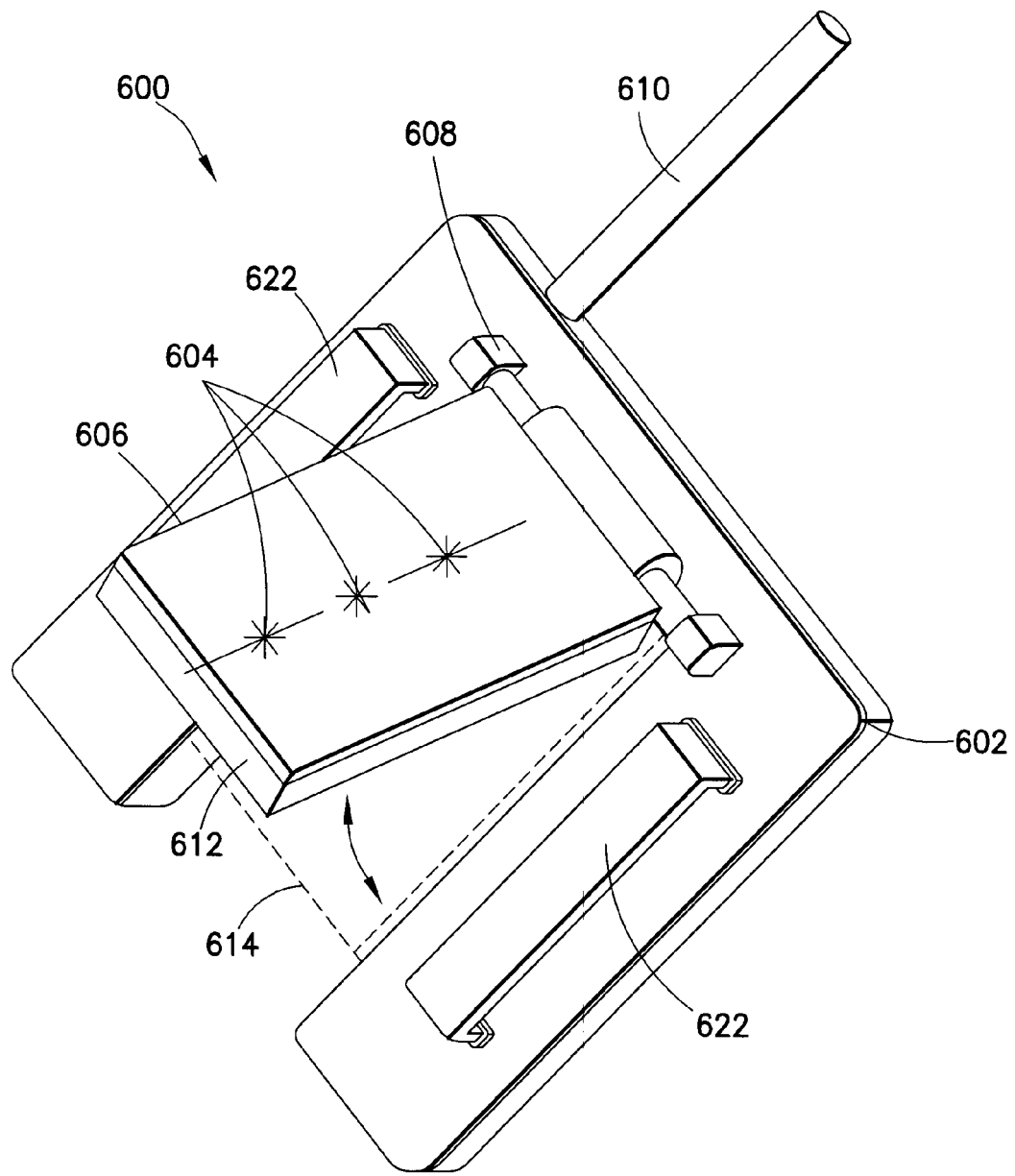
FIG. 6 is a drawing showing a perspective view of a second embodiment of a catheter insertion site contamination reduction device.

As shown in an alternative embodiment 600 depicted in FIG. 6, the light-emitting elements 604 may alternatively or additionally be mounted on a door or flap element 606. The door 606 is movable between an engaged position 614 and a disengaged position 612, and is attached to a hinge 608 which is coupled to the U-shaped housing 602. A biasing mechanism (not shown), such as a spring, may be provided to ensure that the door 606 can be retained in either the engaged position 614 or the disengaged position 612. While the door 606 is in the engaged position 614, the device 600 may be used to illuminate a catheter insertion area. By lifting the door 606 to the disengaged position 612, visual inspection of the catheter insertion area is permitted while the device 600 remains in an installed configuration. In FIG. 6, device 600 is shown powered by power cable 610.

The device 600 may have power and control electronics to provide power to light-emitting elements 604 and to allow control of the device, including switching the light-emitting elements 604 on, timing controls for the light-emitting elements 604, and other necessary control functions. The device 600 may have attachment hooks 622 for holding straps 624 (omitted from FIG. 6 for clarity, but shown in FIGS. 10A and 10B), used to secure the device 600 to a location on a patient's body.

In FIGS. 7-9, catheter insertion site contamination reduction devices are shown in various installed configurations.

In FIG. 7, an installed configuration 702 for contamination reduction device 600 is shown applied directly adjacent to a transparent window dressing 400 as described above. The device 600 is installed at the catheter tube insertion site such that light from the light emitting elements 604 shines through the transparent window 402 of the dressing 400 and directly illuminates the area in the vicinity of the point of insertion 410 of the catheter tube 302 into the body. In this configuration, an adhesive may be deposited on the bottom side of the device 600 for securing the device 600 to the transparent patch 400. Alternatively, a band (not shown) or other manual securing device may be used to hold the contamination reduction device 600 in place. Alternatively, a hook-and-loop reclosable fastener may be used, with one or more patches of hook-and-loop material placed on the patient or the transparent window dressing and one or more patches of hook-and-loop material placed on the device 600 for attachment. Such a hook-and-loop reclosable fastener may be 3M Scotchmate Hook-and-Loop reclosable fastener, or 3M Dual Lock reclosable fasteners, available from 3M Company of Maplewood, Minn., United States.

An alternate installed configuration 802 is depicted in FIG. 8. In this figure, a contamination reduction device 500 possessing angled surfaces 520 is placed a certain distance from the catheter insertion site 302. In this figure, the contamination reduction device 500 is used in conjunction with a transparent window dressing 400 but is not attached directly to the dressing 400. The device 500 may be held in place by a clamp 804 attached to a pole (not pictured) or by another similar device. Holding the device 500 at a distance from the patient's skin helps to reduce heat transfer from the light sources present to the patient's skin, and allows greater overlap of light from different light sources within the housing on the patient's skin, which can lead to greater intensity of light irradiation and thus improved decontamination effectiveness.

An alternate installed configuration 902 is depicted in FIG. 9. A contamination reduction device 500 possessing angled surfaces 520 is placed a certain distance from the catheter insertion site 302. The contamination reduction device 500 is not used in conjunction with any transparent window dressing. Light from light-emitting elements 504 shines directly on the patient's skin.

In any of these embodiments, light may be transmitted from the contamination reduction device to a patient's skin either directly through the air, or via optical conduits. An example of a configuration utilizing a contamination reduction device in conjunction with an optical conduit is shown in FIGS. 10A and 10B.

Figure 10A:
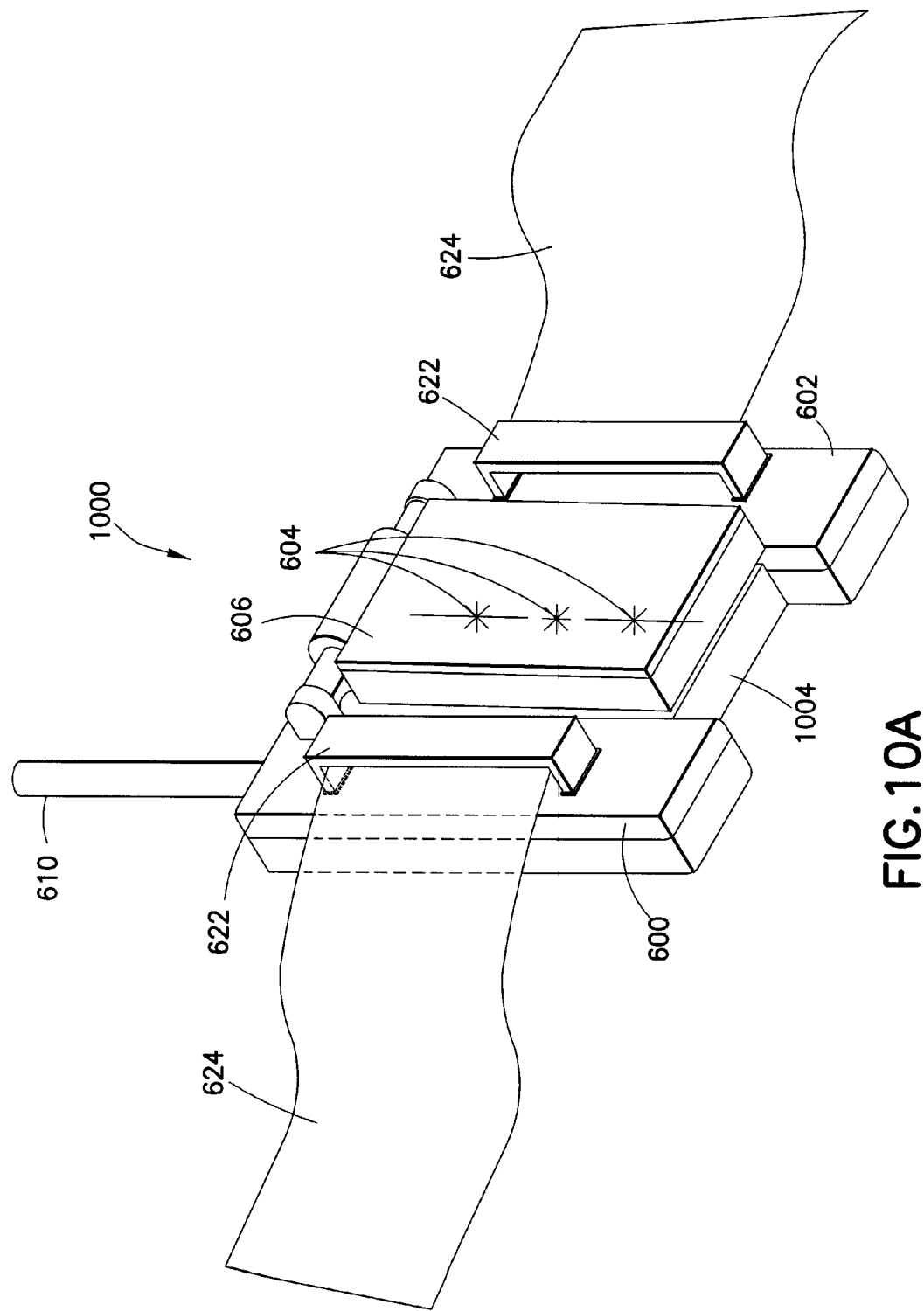
FIG. 10A is a drawing showing a perspective view of a catheter insertion site contamination reduction device together with an optical conduit.
Figure 10B:
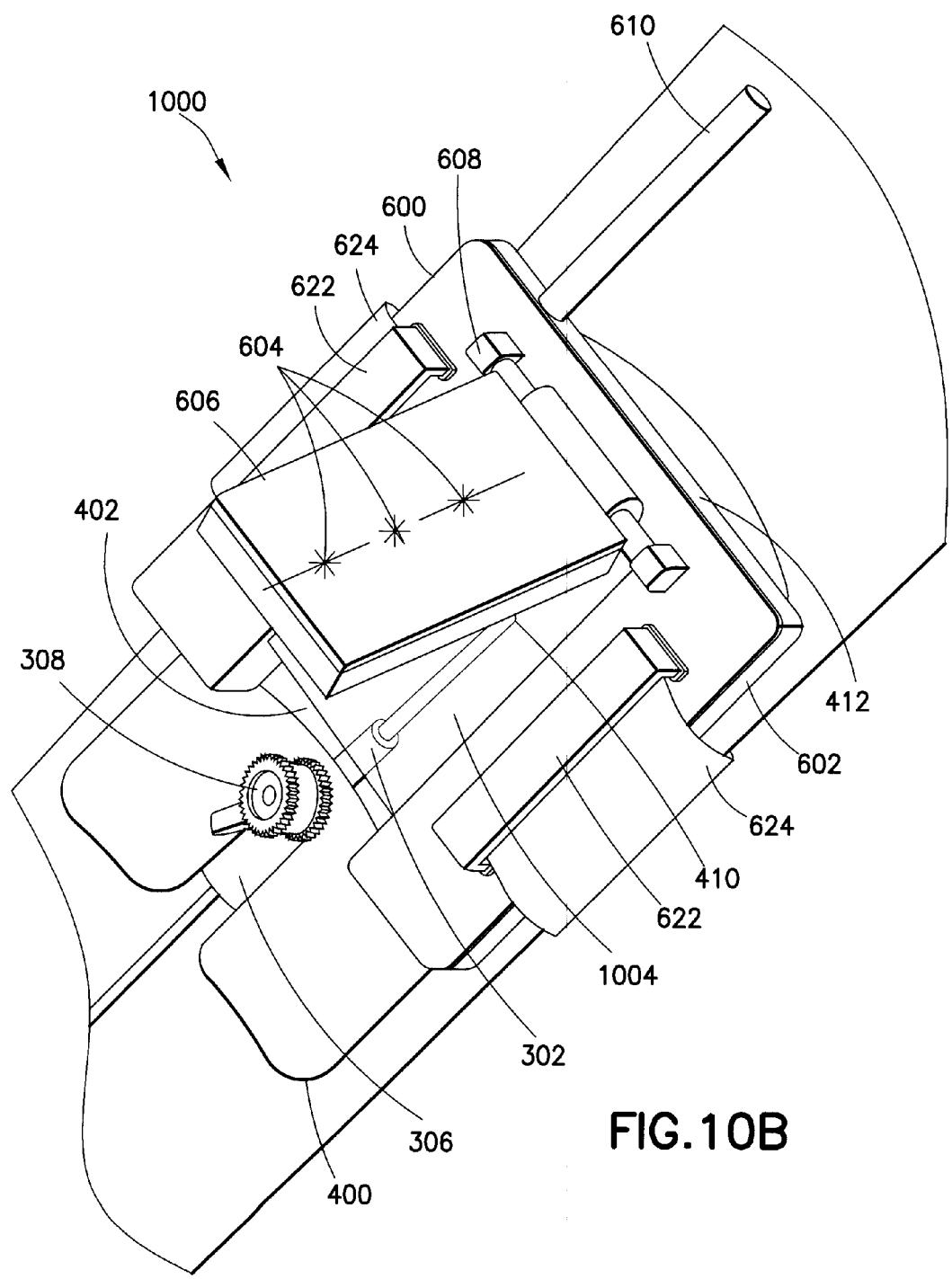
FIG. 10B is a drawing showing a perspective view of a catheter insertion site contamination reduction device installed over a transparent window dressing and used in conjunction with an optical conduit.

In FIGS. 10A and 10B, an alternate installation configuration for a contamination reduction device 1000 is depicted in which an optical conduit 1004 is used. Straps 624, attached to attachment hooks 622, are used to attach device 600 to a patient's arm. Straps 624 are shown in an un-installed configuration in FIG. 10A and in an installed configuration in FIG. 10B. An optical conduit 1004 is useful to ensure better index of refraction matching between the light emitting element(s) and the transparent plastic material of a dressing. Optical conduit 1004 is positioned between the flap element 606 and the transparent window dressing 400. In this figure, the optical conduit 1004 is embodied as a solid rectangular mass placed directly under the flap element 606, such that it can be directly adjacent both to the transparent window 402 of the dressing 400 and to the light-emitting elements 604 within the contamination reduction device 600. The optical conduit 1004 is preferably a resilient transparent material, and may be comprised of any of the following materials: silicon foam, transparent conformable plastic bag filled with a transparent fluid such as saline, or silicone, such as polydimethylsiloxane ("PDMS") silicone, a BISCO® brand silicone, available from Rogers Corporation of Rogers, Conn., USA, such as HT-6240 or MS6000, or ethylene propylene diene Monomer (M-class) rubber ("EPDM"). The optical conduit provides a number of benefits.

First, the optical conduit enhances optical coupling by allowing for efficient transmission of light from light emitting elements to a patient's skin. Because the material used for the transparent window in a transparent window dressing may have a refractive index which differs greatly from that of air, lack of an optical conduit may lead to a high amount of back reflection of emitted light. Use of optical conduits as described above provides a smoother transition in refractive indices from the point at which the light is emitted to the patient's skin.

Second, having the optical conduit may serve as a thermal insulator, which significantly hinders the transfer of heat from the light-emitting elements. Illumination of a patient's skin for long periods of time may cause an uncomfortable buildup of heat, which can be prevented with appropriate use of a thermal insulator. The optical conduit can therefore serve the double purpose of efficient light transfer and blockage of heat transfer. The device, in any of the embodiments presented herein, may also be used with a heat sink, to draw heat away from the light emitting elements.

Operational parameters for the contamination reduction devices disclosed above may be varied to suit different needs. The timing and duration of irradiation, the length of time for which the device is installed, and other timing parameters may be varied depending on the setting in which the irradiation device is to be used. For example, in a hospital setting, the device may be attached continuously, and include a timer for automatic activation. For out-patient use, the device may be used much less frequently, and may be applied to a catheter insertion site only when required, such as several times a day for a short period of only several minutes. The device may include a timer with an alarm or reminder which reminds a patient or caretaker to install and activate the device at pre-scheduled times and for pre-determined periods. Also, the device may include control circuitry configured to control activation timing and activation duration of the light-emitting elements. For example, the control circuitry may be capable of activating the light-emitting elements in one of a variety of timing patterns, including a constant timing pattern, a pulsed timing pattern, a time limited timing pattern, and the like.

The light-emitting diodes used in any of the embodiments disclosed herein may be configured to emit light at roughly the same wavelength as each other, or may be configured such that all lights do not emit roughly the same wavelength as each other.

Additional features may be provided for added convenience. A cradle shaped to conform to the device's geometry may be provided and may act as a charger. The cradle may contain wiring to plug into a wall socket, and may have electrical terminals for connection with and recharging of the device. The cradle may be powered by standard electrical power supply, i.e. 90-240 V and 50-60 Hz. Recharging may start automatically when the device is placed into the cradle and the electrical terminals make contact with the corresponding terminals on the device. The cradle may also use a contact-less recharging mechanism, such as an electrical induction circuit, to recharge the batteries or otherwise provide power to the device. Batteries or other on-board power supply may be rechargeable, and may preferably have at least 96 hours of charge time.

The cradle may also have a port for connection to a computing device. Such a port may be any port capable of providing power and/or data to said housing, such as, for example, a USB port. The device may be controlled through said port, for example, by ordering light-emitting elements on the device on or off. The device may also be monitored, for example, by collecting data regarding how long the device has been on or off, by recording the history of activation of the device (i.e., a history of device usage, including times and durations during which the device has been on or off), and the like.

Preferably, the device is comprised of materials that are lightweight, spill-proof, and that allow the device to be wiped by disinfecting medical fluids such as alcohol and chlorohexidine. The device may have some permanent and some disposable parts. For example, the optical conduit may be disposable. Further, adhesive tape or adhesive components, clamps, or straps/bands used to secure the device to its intended location may be disposable as well.

The device may have buttons and/or indicator lights for power, control and various indications. A single on/off push-button, or on button and off button may be provided on the device. Indicators lights indicating that the device is currently providing illumination, that the device is currently charging, and that battery or other on-board power is low may also be provided. The device may also include displays indicating the time elapsed from last illuminating sequence, an illumination sequence selector for selecting a pre-set or pre-programmed illumination sequence, and a small switch for turning light emitting elements off when the door 606 is in a disengaged position.

The structures disclosed herein also have application in systems wherein the bactericidal radiation is light having a wavelength outside the violet/blue spectral region.

Although described as used in the context of a peripheral venous catheter, due to the fact that items which penetrate the body and remain in such a position for a prolonged period of time may present a risk of infection, it is contemplated that the contamination reduction device disclosed herein may be used with any element that projects into a human body, including other types of catheters, orthopedic pins, or other types of needles, pins or tubes that are inserted into a patient's skin, or any other like device.

While the invention has been described with reference to various embodiments, it will be understood by those skilled in the art that various changes may be made and equivalents may be substituted for elements thereof without departing from the scope of the invention. In addition, many modifications may be made to adapt a particular situation to the teachings of the invention without departing from the essential scope thereof. Therefore it is intended that the invention not be limited to the particular embodiment disclosed as the best mode contemplated for carrying out this invention.

We claim:

1. An apparatus for preventing infection at a catheter insertion site, comprising:
   a U-shaped housing comprising a cross-bar and a pair of arms extending from said cross-bar, and light-emitting elements for irradiating a catheter insertion site with violet and/or blue light having wavelengths in a range of 390-492 nanometers;
   said cross-bar and said pair of arms having a diagonal lower surface from which one or more of said light-emitting elements extend;
   said light-emitting elements positioned such that they emit light in a direction below the housing while operational.

2. The apparatus of claim 1, further comprising:
   strap slots and a strap for attaching the apparatus to a catheter insertion site, the strap slots extending from a top of the housing.

3. The apparatus of claim 1, further comprising:
   a catheter inserted into said catheter insertion site;
   a transparent window dressing affixed over the catheter insertion site;
   said light-emitting elements positioned such that they emit light through said transparent window dressing.

4. The apparatus of claim 1, further comprising:
   batteries located within said pair of arms, the batteries configured to provide power to said light-emitting elements.

5. The apparatus of claim 1, further comprising:
   a clamp holding the U-shaped housing above the catheter insertion site.

6. The apparatus of claim 1, further comprising:
   an electronic cable connected to the housing, and configured to provide power to the light-emitting elements.

7. The apparatus of claim 1, further comprising control circuitry configured to control activation timing and activation duration of said light-emitting elements.

8. The apparatus of claim 1, wherein:
   said light-emitting elements are all configured to emit light at roughly the same wavelength as each other.

9. The apparatus of claim 1, wherein:
   said light-emitting elements are all configured to emit light which is not at roughly the same wavelength as each other.

10. The apparatus of claim 1, further comprising:
    a heat sink coupled to the U-shaped housing, configured to draw heat from the light-emitting elements and emit said heat into the atmosphere, to reduce the temperature of said light-emitting elements.

11. An apparatus for preventing infection at a catheter insertion site, comprising:
    a U-shaped housing comprising a cross-bar and a pair of arms extending from said cross-bar, and light-emitting elements for irradiating a catheter insertion site with violet and/or blue light having wavelengths in a range of 390-492 nanometers;
    a flap element hingedly attached to said cross-bar between said pair of arms and movable between an engaged position where the flap element is positioned in a plane corresponding to a horizontal plane of the said pair of arms and a disengaged position where the flap element is lifted up from the horizontal plane of said pair of arms, said light-emitting elements being located on said flap element, said light-emitting elements positioned such that they emit light in a direction below the housing while operational, said flap element being biased towards said engaged position in which the light from the light-emitting elements is directed directly downward; and an optical conduit configured to enhance optical coupling between said light-emitting elements and said catheter insertion site, and configured to act as a thermal insulator, said optical conduit located between the pair of arms and positioned such that it is directly below the flap element when the flap element is in said engaged position, said optical conduit being composed of an optically transmissive material for allowing light emitted from said light-emitting elements to be incident on said catheter insertion site.

12. The apparatus of claim 11, further comprising:

strap slots and a strap for attaching the apparatus to a catheter insertion site, the strap slots extending from a top of the housing.

13. The apparatus of claim 11, further comprising:

a catheter inserted into said catheter insertion site;

a transparent window dressing affixed over the catheter insertion site;

said light-emitting elements positioned such that they emit light through said transparent window dressing.

14. The apparatus of claim 13, wherein:

said optical conduit is adjacent to said transparent window dressing and a bottom surface of said flap element when said flap element is in said engaged position.

15. The apparatus of claim 11, further comprising:

an adhesive holding the U-shaped housing above the catheter insertion site.

16. The apparatus of claim 11, further comprising:

an electronic cable connected to the housing, and configured to provide power to the light-emitting elements.

17. The apparatus of claim 11, wherein the light-emitting elements are light emitting diodes.

18. The apparatus of claim 11, further comprising:

a cradle for receiving said U-shaped housing, said cradle having a charging mechanism capable of being coupled with said U-shaped housing, to provide power to said U-shaped housing.

19. The apparatus of claim 18, wherein:

said cradle further comprises a port for connection to a computer for control and data gathering purposes.

20. A method of preventing infection at a catheter insertion site, comprising:

inserting a catheter into a catheter insertion site;

applying a transparent window dressing to said catheter insertion site;

providing an apparatus for preventing infection at a catheter insertion site, said apparatus comprising a U-shaped housing having light-emitting elements directed in a downward direction for irradiating the catheter insertion site with violet and/or blue light having wavelengths in a range of 390-492 nanometers; and introducing said apparatus for preventing infection over said transparent window dressing such that said light-emitting elements are directed to emit light through said transparent window dressing.

21. The method of claim 20, further comprising:

moving a flap element attached to a cross-bar of said U-shaped housing between a pair of arms extending from the cross-bar from a disengaged position where the flap element is positioned in a plane that does not correspond to a horizontal plane of said pair of arms to an engaged position where the flap element is positioned in a plane that corresponds to the horizontal plane of said pair of arms to activate the device such that light from said light-emitting elements are directed at said catheter insertion site.

22. The method of claim 21, wherein:

introducing said apparatus comprises applying an adhesive to said apparatus and applying said apparatus so said catheter insertion site such that said adhesive holds said apparatus in place.

23. The method of claim 21, wherein:

introducing said apparatus comprises utilizing a clamp to hold said apparatus in place over said catheter insertion site such that light from said light-emitting elements is incident on said catheter insertion site.

24. The method of claim 21, further comprising:

periodically providing a reminder to activate the device at pre-scheduled times and for pre-determined periods.

25. The method of claim 21, further comprising:

providing an optical conduit above said transparent window dressing.

26. The method of claim 21, wherein:

introducing said apparatus comprises utilizing a hook-and-fastener material to hold said apparatus in place over said catheter insertion site such that light from said light-emitting elements is incident on said catheter insertion site.

* * * * *